(12) United States Patent
Santanello

(10) Patent No.: US 10,279,087 B2
(45) Date of Patent: May 7, 2019

(54) MINIMALLY INVASIVE SUCTION SLEEVE

(71) Applicant: Santanello Surgical, LLC, Columbus, OH (US)

(72) Inventor: Steven Santanello, Columbus, OH (US)

( * ) Notice: Subject to any disclaimer, the term of this patent is extended or adjusted under 35 U.S.C. 154(b) by 305 days.

(21) Appl. No.: 15/250,801

(22) Filed: Aug. 29, 2016

(65) Prior Publication Data

US 2017/0056571 A1 Mar. 2, 2017

Related U.S. Application Data

(60) Provisional application No. 62/212,683, filed on Sep. 1, 2015.

(51) Int. Cl.
*A61M 31/00* (2006.01)
*A61M 1/00* (2006.01)
*A61M 25/00* (2006.01)
*A61M 27/00* (2006.01)

(52) U.S. Cl.
CPC .......... *A61M 1/008* (2013.01); *A61M 1/0086* (2014.02); *A61M 25/007* (2013.01); *A61M 2205/586* (2013.01)

(58) Field of Classification Search
CPC ........ A61M 31/00; A61M 25/00; A61M 1/00; A61M 27/00
See application file for complete search history.

(56) References Cited

U.S. PATENT DOCUMENTS

| | | |
|---|---|---|
| 1,879,249 A | 9/1932 | Honsaker |
| 2,930,378 A | 3/1960 | Buyers |
| 3,042,044 A | 7/1962 | Sheridan |
| 3,108,595 A | 10/1963 | Overment |
| 3,314,430 A | 4/1967 | Alley et al. |
| 3,528,427 A | 9/1970 | Argyle et al. |
| 3,677,243 A * | 7/1972 | Nerz ................. A61M 25/0668 604/161 |
| 4,069,814 A | 1/1978 | Clemens |
| 4,146,034 A * | 3/1979 | Gupta ............... A61M 16/0463 128/207.14 |
| 4,451,257 A | 5/1984 | Atchley |
| 4,487,600 A | 12/1984 | Brownlie et al. |
| 4,767,404 A | 8/1988 | Renton |
| 4,867,747 A | 9/1989 | Yarger |
| 5,019,039 A | 5/1991 | Anderson |

(Continued)

*Primary Examiner* — Tatyana Zalukaeva
*Assistant Examiner* — Ilya Y Treyger
(74) *Attorney, Agent, or Firm* — Notre Dame Intellectual Property Clinic

(57) ABSTRACT

A minimally invasive surgery suction sleeve configured for use with an inner cannula of a suction instrument. The sleeve includes a first opening at a proximal end, a second opening at a distal end, and a tube between the first opening and the second opening. The sleeve slides over a suction instrument. The distal end is configured to insert into the body and includes a plurality of apertures that provide for pool suction. The sleeve further includes a flange at the proximal end that allows a surgeon to manipulate the sleeve, switching between spot and pool mode by sliding the sleeve over the inner cannula of the suction instrument. In spot mode, the tip of the suction instrument is exposed. In pool mode, the sleeve slides forward, covering the tip of the suction instrument so that fluent material is drawn through the apertures in the sleeve.

8 Claims, 15 Drawing Sheets

(56) References Cited

U.S. PATENT DOCUMENTS

| | | | |
|---|---|---|---|
| 5,295,956 A | 3/1994 | Bales | |
| 5,379,650 A * | 1/1995 | Kofoed | G01F 1/363 |
| | | | 600/538 |
| 5,505,710 A * | 4/1996 | Dorsey, III | A61M 1/008 |
| | | | 604/158 |
| 5,827,218 A | 10/1998 | Nguyen et al. | |
| 6,733,479 B1 | 5/2004 | Ott | |
| 2006/0259014 A1 | 11/2006 | Yarger | |
| 2008/0015527 A1 | 1/2008 | House | |
| 2009/0005741 A1 | 1/2009 | Martin et al. | |

\* cited by examiner

MINIMALLY INVASIVE SUCTION SLEEVE

CROSS-REFERENCE TO RELATED APPLICATIONS

This application claims the benefit of the filing date of U.S. provisional patent application Ser. No. 62/212,683, filed on Sep. 1, 2015, entitled "Laparoscopic Poole Suction Catheter," the disclosure of which is incorporated herein by reference.

BACKGROUND

In the past decade, laparoscopic surgery, or minimally invasive surgery of the chest and abdomen, has permeated the medical field. Over seven million laparoscopic procedures are performed annually in the United States. Types of laparoscopic procedures have continued to expand and now include procedures for all organ systems. Differing from traditional open surgery, laparoscopic surgery involves several small incisions versus one large incision. Advantages include reduced hospital stays, less pain and shorter recovery times. The incisions, each measuring approximately 0.5 cm-1.5 cm, are called port sites. The incisions hold an introducer port through which a fiber optic camera and specialized laparoscopic instruments are inserted into the body cavity. Instruments are designed to replicate the ergonomics and function of their open surgery counterparts within the context of the limitations of introducer ports and laparoscopic requirements to allow for intuitive use.

A simple, but necessary, function in most surgeries is the ability to efficiently suction fluids from the body cavity and around the surgical site. Spot suctioning, which is the suctioning from the tip of a suction instrument, is particularly useful when the fluid is localized and free of surrounding debris and tissue. It has inherent drawbacks when large volumes of fluid surround organs as the tip is likely to become occluded. To resolve this issue, a pool suction instrument was developed and has had long-standing use in open surgical cases. The pool suction instrument has an inner cannula for direct spot suctioning and an outer-sleeve with multiple holes, where the outer-sleeve covers the inner cannula. When the inner cannula is covered, fluid drains through the multiple holes and is suctioned through the inner cannula. This reduces the chance of clogging and allows for the efficient suctioning of large volumes of fluid.

BRIEF SUMMARY

The following presents a simplified summary in order to provide a basic understanding of some aspects of the claimed subject matter. This summary is not an extensive overview. It is not intended to either identify key or critical elements or to delineate the scope of the claimed subject matter. Its sole purpose is to present some concepts in a simplified form as a prelude to the more detailed description that is presented later.

A sleeve for use with a minimally invasive surgery suction instrument, comprising a tube having an inner lumen configured to receive an inner cannula of the suction instrument and allow the inner cannula to translate freely within the inner lumen. The sleeve also comprises a distal end of the tube configured to insert into an introducer port, the distal end having a plurality of radially facing apertures and an axially facing opening and a proximal end connected to the tube and configured to facilitate grasping and manipulation by a user to translate the sleeve between a first position and a second position. In the first position, a distal tip of the inner cannula is exposed beyond the axially facing opening of the tube and in the second position the distal tip of the inner cannula is seated within the inner lumen of the tube, proximal to the radially facing apertures. In other embodiments, the sleeve also comprises a flange that extends radially from the proximal end, wherein force exerted on the flange in a direction longitudinal to the tube causes the sleeve to translate from the first position to the second position.

A method of providing suction during a surgical procedure is also described. The method comprising providing a sleeve that slides onto an inner cannula of a suction instrument, the sleeve having a tube having an inner lumen configured to receive an inner cannula of the suction instrument and allow the inner cannula to translate freely within the inner lumen; a distal end of the tube configured to insert into an introducer port, the distal end having a plurality of radially facing apertures and an axially facing opening; and a proximal end configured to facilitate manipulation by a user. The method further comprises sliding the sleeve onto the inner cannula of the suction instrument, where the inner cannula is disposed within the inner lumen of the sleeve; inserting the distal end of the sleeve with the inner cannula through an introducer port into a body; manipulating the proximal end of the sleeve to extend the radial apertures over a distal tip of the inner cannula to provide pool mode suction; and manipulating the proximal end of the sleeve to extend the distal tip of the inner cannula beyond the distal end of the sleeve to transition to spot mode suction, where the transition between pool mode and spot mode occurs while the sleeve and suction instrument are seated within the introducer port. In additional embodiments, the distal end of the sleeve includes a channel on an exterior of the distal end, the channel connected to at least one of the plurality of apertures and fluent material is directed to at least one of the plurality of apertures via the channel.

To the accomplishment of the foregoing and related ends, certain illustrative aspects of the claimed subject matter are described herein in connection with the following description and the annexed drawings. These aspects are indicative of various ways in which the subject matter may be practiced, all of which are intended to be within the scope of the claimed subject matter. Other advantages and novel features may become apparent from the following detailed description when considered in conjunction with the drawings.

BRIEF DESCRIPTION OF THE DRAWINGS

The systems, devices and methods may be better understood by referring to the following description in conjunction with the accompanying drawings, in which like numerals indicate like structural elements and features in various figures. The components in the figures are not necessarily to scale, and simply illustrate the principles of the systems, devices and methods. The accompanying drawings illustrate only possible embodiments of the systems, devices and methods and are therefore not to be considered limiting in scope.

DETAILED DESCRIPTION

Aspects of the system and methods are described below with reference to illustrative embodiments. The references to illustrative embodiments below are not made to limit the scope of the claimed subject matter. Instead, illustrative embodiments are used to aid in the description of various aspects of the systems and methods. The description, made by way of example and reference to illustrative reference is not meant to being limiting as regards any aspect of the claimed subject matter.

Current suction instruments are unsatisfactory for use during minimally invasive surgery. During minimally invasive surgery, the instrument resides almost entirely within the body. Therefore, only the proximal end of the suction instrument and suction sleeve, the end not inserted into the body, is manipulable by the surgeon or surgical team when the instrument is in use. A suction instrument that includes pool as well as spot suctioning, but where instrument must be removed and reinserted in order to switch between a spot suction and pool suction mode has severe drawbacks. This is inconvenient for the surgeon, who must simultaneously operate other surgical devices, and increases the duration of the surgery and chance of unnecessary harm to the patient. Therefore, there are significant advantages to a sleeve that is manipulable using only the proximal end of the sleeve, and which can switch between spot and pool modes without removal from the body.

Figure 1:
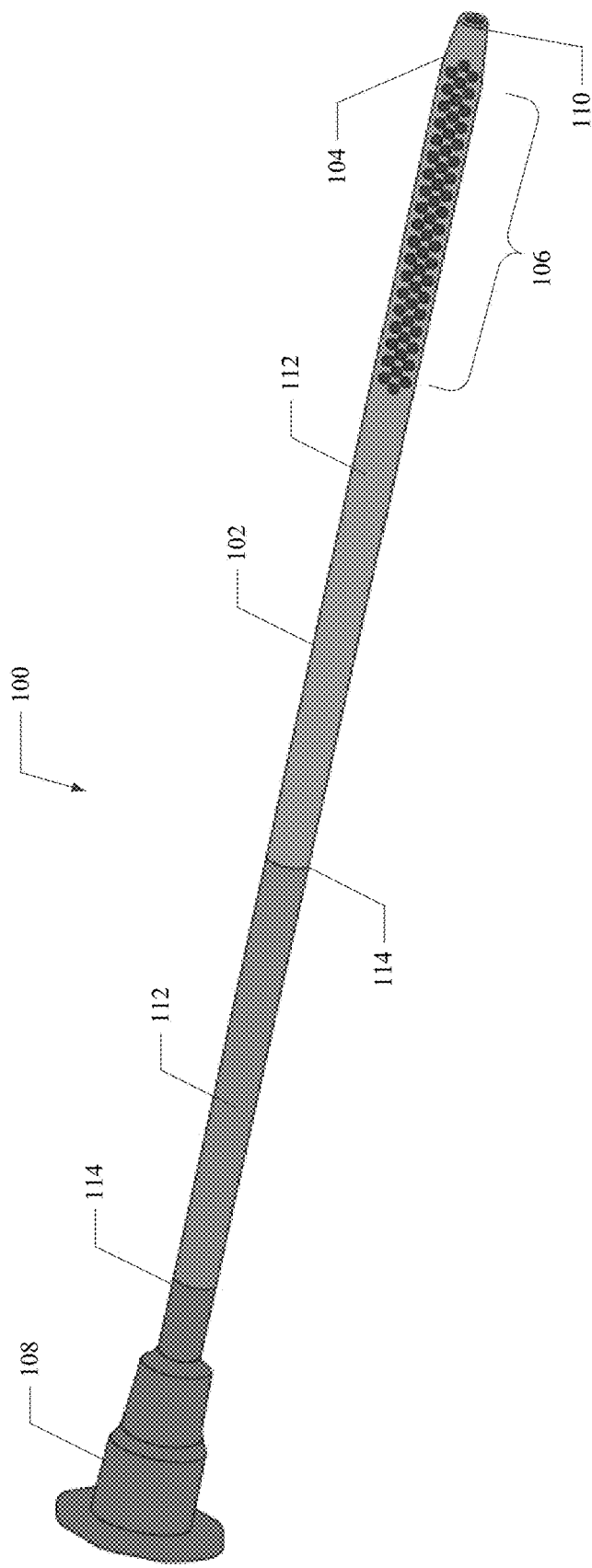
FIG. 1 depicts a perspective view of an embodiment of a suction sleeve.
Figure 4:
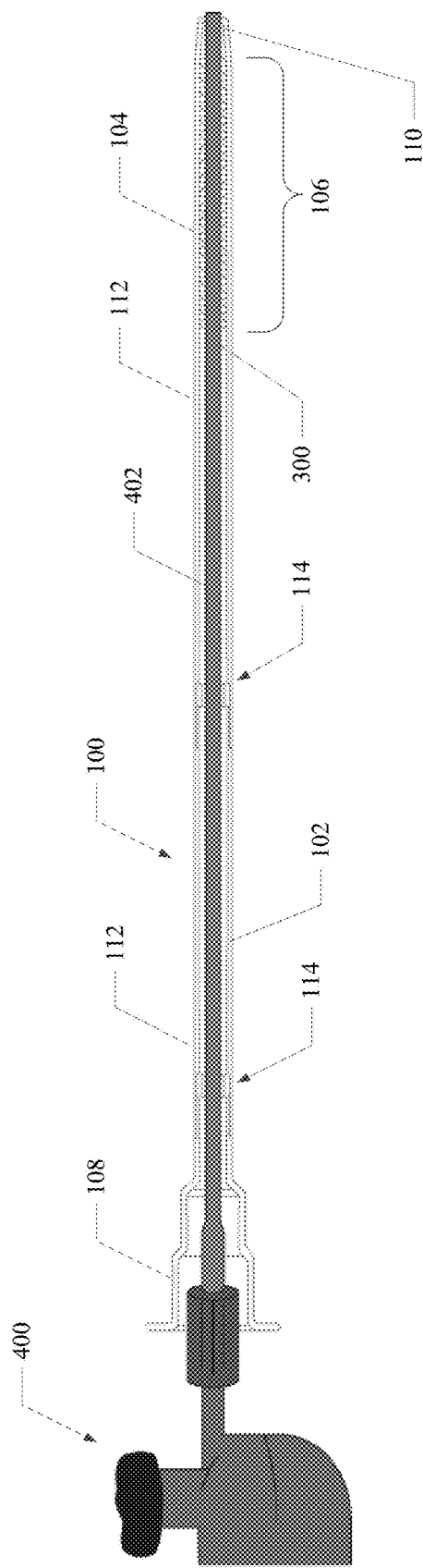
FIG. 4 depicts the suction sleeve of FIG. 1 mounted on a minimally invasive surgery suction instrument.

Referring now to FIG. 1, an embodiment of a suction sleeve 100 is depicted. The illustrated sleeve 100 is configured to permit the surgeon to switch between pool and suction mode without removal of the suction instrument 400 from the introducer port and the body. As can be seen in FIG. 4, a suction instrument 400 can be inserted into the depicted suction sleeve 100. In embodiments, the suction instrument 400 is a spot suction instrument 400, and the suction sleeve 100 and suction instrument 400 are shaped and sized to pass through an introducer port to provide suction within a body during laparoscopic surgery.

As depicted, the suction sleeve 100 includes a hollow tube 102 into which the suction instrument 400 is inserted, a distal end 104 that is inserted through the introducer port into the body, and a proximal end 108 that is grasped by a member of the surgical team. As used herein, the term "tube" indicates a long, hollow object that can be, but is not limited to, the cylindrical shape. The distal end 104 of the suction sleeve 100 includes a plurality of apertures 106, through which fluent material is drawn when the suction sleeve 100 is in use in pool mode. In embodiments, the apertures 106 are configured radially on the sleeve 100. Potential numbers and configurations of the apertures 106 are discussed in greater detail below, but in one embodiment the apertures 106 are configured for pool suction. The proximal end 108 of the suction sleeve 100 is shaped to allow a surgeon or user to grasp and manipulate the suction sleeve 100. Descriptions of the use of the suction sleeve 100 herein are described with respect to use by a surgeon for simplicity; however, use of the device is not limited to a surgeon and the suction sleeve 100 can be used by any member of a surgical team.

Figure 5:
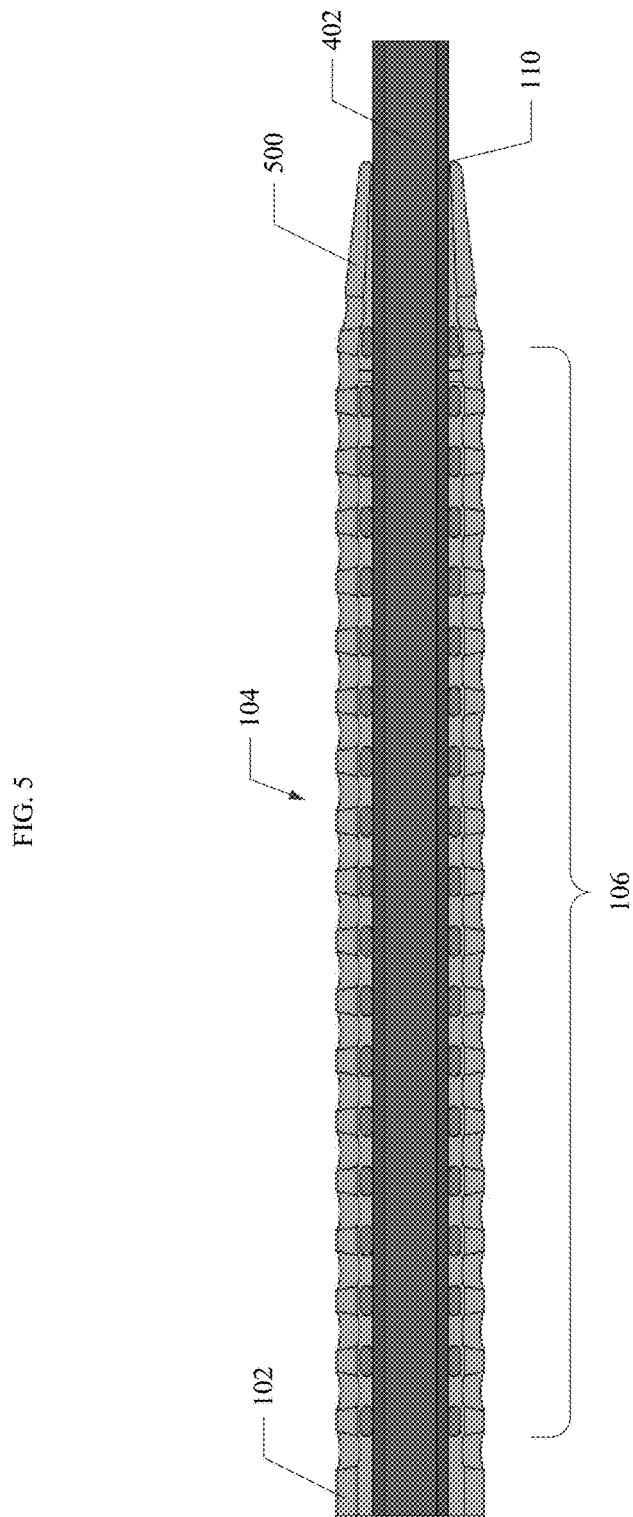
FIG. 5 depicts a sectional view of the distal end of an embodiment of a suction sleeve and an inner cannula of a suction instrument in spot mode.

When the suction sleeve 100 and suction instrument 400 are deployed during surgery, the suction sleeve 100 slides relative to the suction instrument 400 to transition between at least two different modes of suction operation. First, in spot suction mode, the distal tip of the suction instrument 400 is exposed by retracting the distal end 104 of the suction sleeve 100 to expose the distal tip of the suction instrument 400, as shown in FIG. 5. In this mode, the suction instrument 400 functions as a conventional spot suction instrument 400, drawing fluid or fluent material through the distal tip of the suction instrument 400.

Figure 6:
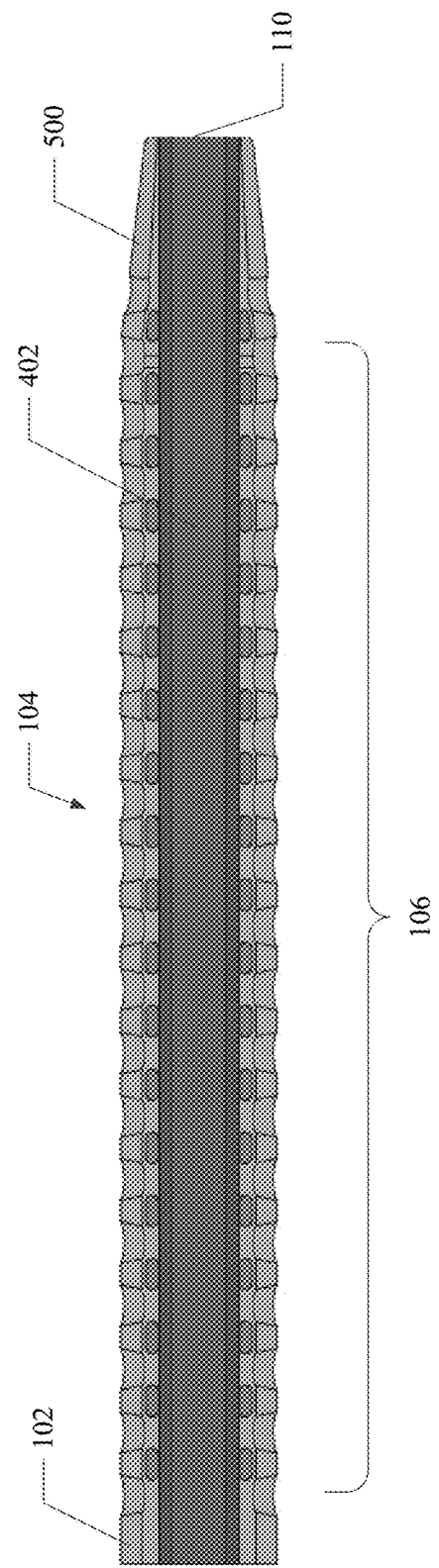
FIG. 6 depicts a sectional view of the distal end of an embodiment of a suction sleeve and the inner cannula of a suction instrument in pool mode.

In a second mode, referred to herein as "pool mode", the suction sleeve 100 slides relative to the suction instrument 400, and the distal tip of the suction instrument 400 is seated within the suction sleeve 100, as shown in FIG. 6. In pool mode, suction from the suction instrument 400 draws fluent material through the apertures 106 in the suction sleeve 100. Here, the number and configuration of the apertures 106 reduce the potential for the suction instrument 400 to clog during operation in comparison to spot mode.

In embodiments, the suction sleeve 100 and suction instrument 400 can switch between pool mode and spot mode by sliding the suction sleeve 100 axially relative to the suction instrument 400. As shown, the proximal end 108 of the suction sleeve 100 is shaped to allow the surgeon to manipulate the sleeve 100 using a single hand. As discussed in greater detail below, a surgeon can grasp the suction instrument 400 with suction sleeve 100 in one hand and use one or more fingers of that hand to slide the suction sleeve 100 relative to the suction instrument 400, switching between pool and spot mode without requiring the use of a second hand. In addition, transition between modes can be performed without necessitating the removal of the suction sleeve 100 and suction instrument 400 from the introducer port or surgical field. The result is a flexible, easy to use suction system that a surgeon can control single-handedly.

Referring once again to in FIG. 1, an embodiment of the sleeve 100 includes a tube 102, a proximal end 108 and a distal end 104. As depicted in FIG. 4, for laparoscopic surgery a minimally invasive surgery suction instrument 400 is inserted into the sleeve 100. The distal end 104 of the sleeve 100 is inserted into the body cavity through an incision and introducer port. In this embodiment, the distal end 104 includes an axial opening 110 and a plurality of apertures 106, facing radially outward, which allow for fluent material to be drawn away from the laparoscopic surgery site when the sleeve 100 is coupled with the suction instrument 400. The proximal end 108 of the sleeve 100 remains outside of the patient's body and is configured to be grasped and manipulated by the user. In the illustrated embodiment, the proximal end 108 includes a plurality of annular ledges that cooperate with the suction instrument 400 to control movement of the sleeve 100 relative to the suction instrument 400 and a flange 706 that facilitates sliding the sleeve 100 axially relative to the suction instrument 400. In this embodiment, the sleeve 100 includes a plurality of segments 112 joined by a plurality of connectors 114. While the illustrated embodiment shows a sleeve 100 formed from three separate segments 112, the sleeve 100 can be monolithic, or formed from any number of segments 112 as desirable based upon manufacturing needs, ease of use, or cleaning and sterilization of the sleeve 100.

Figure 2:
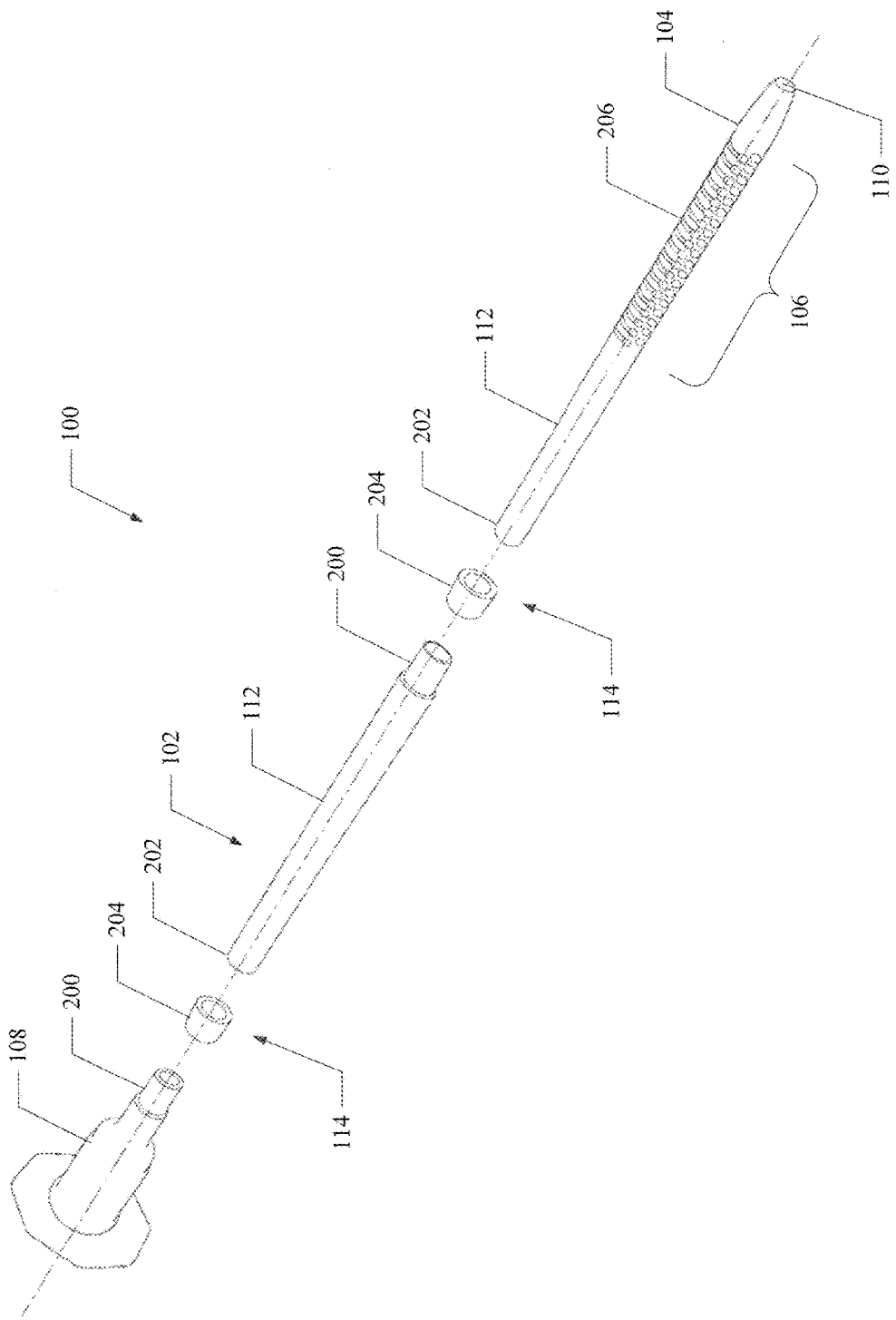
FIG. 2 depicts an exploded, perspective view of another embodiment of a suction sleeve.

FIG. 2 is an exploded view of an embodiment of the sleeve 100. As shown, the tube 102 of the depicted sleeve 100 is hollow and the sleeve 100 is formed from three segments 112. In this embodiment, the tube 102 includes segments 112 that are joined via a plurality of connectors 114, each connector 114 including an inner connection member 200 and outer connection member 202 and an O-ring 204. Here, the O-ring 204 is seated within the outer connection member 202 of the tube 102 and the inner connection member slides into the outer connection member 202. This embodiment of the connector 114 is shown and described in greater detail below in FIGS. 9-12.

FIG. 2 also shows one or more channels 206 formed in the distal end 104 of the sleeve 100 between or among the apertures 106. These channels 206 are configured to direct the flow of fluent material to the apertures 106. In addition, the channels 206 can prevent the suction from forming a seal with surrounding tissue at one or more of the apertures 106 during a surgical procedure. During use, if an aperture is proximate to or abuts tissue, the tissue may connect with the entirety of the edge of the aperture 106, forming a seal. When a seal is formed, the aperture 106 fails to draw fluent material, reducing effectiveness of the suction instrument 400. A channel 206 connected to one or more apertures 106, creates an uneven surface, making it more difficult for a seal to form. And, even in the absence of a seal, a channel 206 makes it more likely that the aperture 106 will continue to draw fluent material even when an aperture 106 is partially or totally obscured by tissue. In the illustrated embodiment these channels 206 connect two or more apertures 106, extending circumferentially around at least part of the distal end 104. However, any configuration and number of channels 206 can be used.

Figure 3:
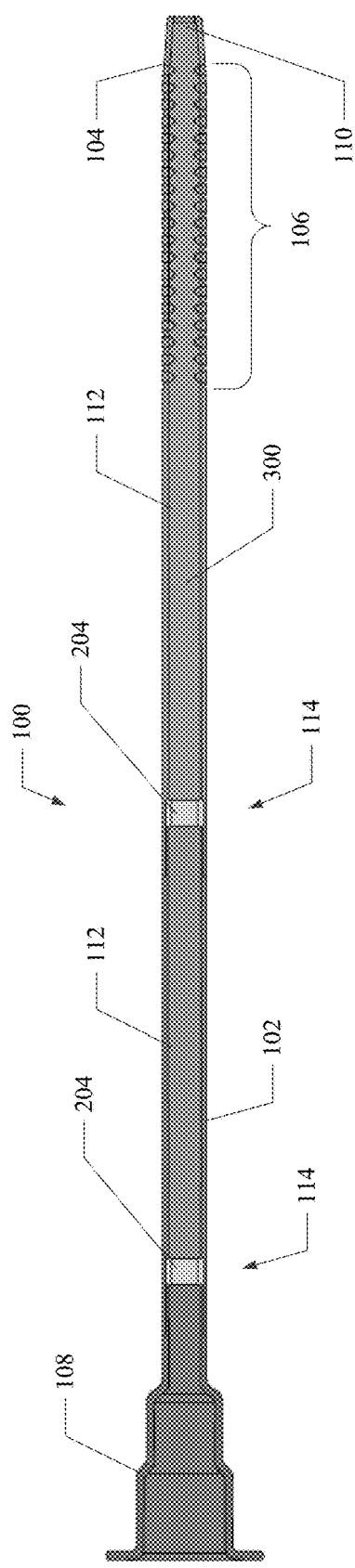
FIG. 3 depicts a sectional view of the embodiment of the suction sleeve of FIG. 1.

Referring now to FIG. 3, a cross-section of an embodiment of the sleeve 100 is depicted. As shown, the sleeve 100 is hollow and has an inner lumen 300 through which an inner cannula 402 of a suction instrument 400 may be placed. The inner lumen 300 has a diameter that is sufficient to house the corresponding diameter of the inner cannula 402, yet provides a lateral margin permitting the sleeve 100 to freely translate along the axis of the inner cannula 402. It is this movement that allows easy transition between spot and pool mode. As shown in the cross-section illustrated in FIG. 3, one or more O-rings 204 are seated within the outer connection member 202 when the sleeve 100 is assembled. The inner cannula 402 is inserted through these O-rings 204 and, as described in more detail below with respect to FIGS. 9-12, the O-rings 204 can stabilize the inner cannula 402 within the sleeve 100, reducing the potential for excess lateral movement within the sleeve 100. This increases control over the inner cannula 402 as well as the suction instrument 400 and sleeve 100 in general by the surgeon. In addition, friction between the O-ring 204 and the inner cannula 402 can prevent unintended axial movement of the sleeve 100 relative to the suction instrument 400.

FIG. 4 depicts an example application of an embodiment of a suction sleeve 100, where the sleeve 100 is mounted on a suction instrument 400. Typically, suction instruments 400 include one or more switches that control suction and delivery of fluid. The suction instrument 400 includes an inner cannula 402, which passes through the inner lumen 300 of the sleeve 100. The tip of the inner cannula 402 can provide spot suctioning when it extends beyond the distal end 104 of the sleeve 100. The suction instrument 400 is connected with a suitable means for establishing a drain flow from the surgical field, such as a source of negative pressure or the like.

This embodiment of the suction sleeve 100 and suction instrument 400 can switch between pool mode and spot mode by sliding the suction instrument 400 axially within the suction sleeve 100. The proximal end 108 of the sleeve 100, as embodied here, can be manipulated by one of the user's fingers while the suction instrument 400 can be held with the remainder of the hand, allowing for operation of the device with a single hand. Manipulation of the sleeve 100 with one or more fingers can leave the remainder of the surgeon's digits and hand free to manipulate the suction instrument 400. A skilled surgeon will be able to adjust the position of the device, engage suction or fluids, and control pool or spot suction mode, using a single hand and virtually simultaneously.

FIG. 5 and FIG. 6 provide a close view of the distal end 104 of an embodiment of the sleeve 100 mounted on an inner cannula 402 of a suction instrument 400. The figures show two different modes of operation for the sleeve 100 and suction instrument 400. In spot mode, illustrated by FIG. 5, the inner cannula 402 of the suction instrument 400 extends through the distal axial opening 110 of the sleeve 100, providing for a localized drain. As shown in this embodiment, the distal end 104 comprises a tapered tip 500 having an area of decreasing diameter which terminates at the distal axial opening 110, where the distal axial opening 110 is generally of a size and shape to receive the distal tip of the inner cannula 402. The distal axial opening 110 provides support and guidance to the inner cannula 402. The tapered tip 500 assists in delivering the inner cannula 402 to narrow areas or cavities within the body to drain fluent material. Because the tip of the inner cannula 402 extends beyond the end of the sleeve 100 in this mode, the suction draws fluent material through the aperture or apertures at the tip of the inner cannula 402 rather than through the apertures 106 in the sleeve 100.

In pool mode, as illustrated by FIG. 6, the sleeve 100 is positioned relative to the suction instrument 400 such that the distal tip of the inner cannula 402 of the suction instrument 400 is within hollow tube 102 proximate to the distal end 104 of the sleeve 100, allowing for fluent material to be drawn through the plurality of apertures 106, facing radially outward, as well as the distal axial opening 110. The number of apertures 106 and the spread of apertures 106 over a wider area decreases the risk of total blockage of the suction instrument 400. During pool mode operation, fluent material will pass through the apertures 106 or the distal axial opening 110 prior to being drawing into the inner cannula 400, making it unlikely that the inner cannula 400 will become occluded. Although the inner cannula 402 is illustrated almost flush with the end of the sleeve 100, in pool mode the inner cannula 402 may be drawn further into the sleeve 100 so that the end of the sleeve 100 extends well past the end of the inner cannula 402.

Because this embodiment of the sleeve 100 can translate freely along the axis of the inner cannula 402, it is possible for the surgeon to alternate between spot and pool suction mode during laparoscopic surgery without removing the suction instrument 400 or sleeve 100 from the introducer port or surgical site. This ability to switch seamlessly from pool to spot mode without removing the instrument 400 gives the surgeon greater flexibility and reduces the time necessary to complete the surgical procedure. This also results in increased suctioning efficiency and reduces surgeon frustration.

Figure 7:
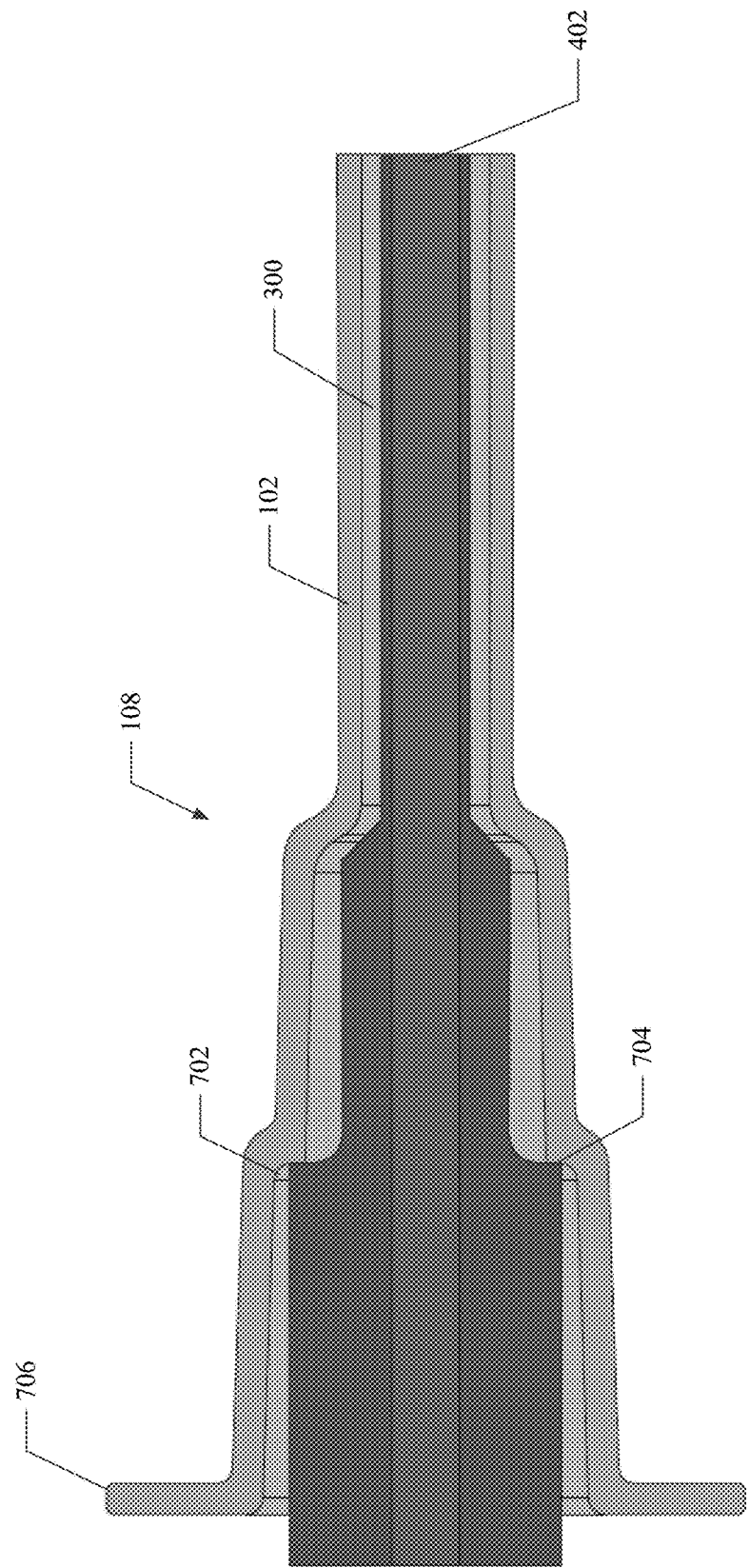
FIG. 7 depicts a sectional view of the proximal end of an embodiment of a suction sleeve and the inner cannula of a suction instrument.
Figure 8:
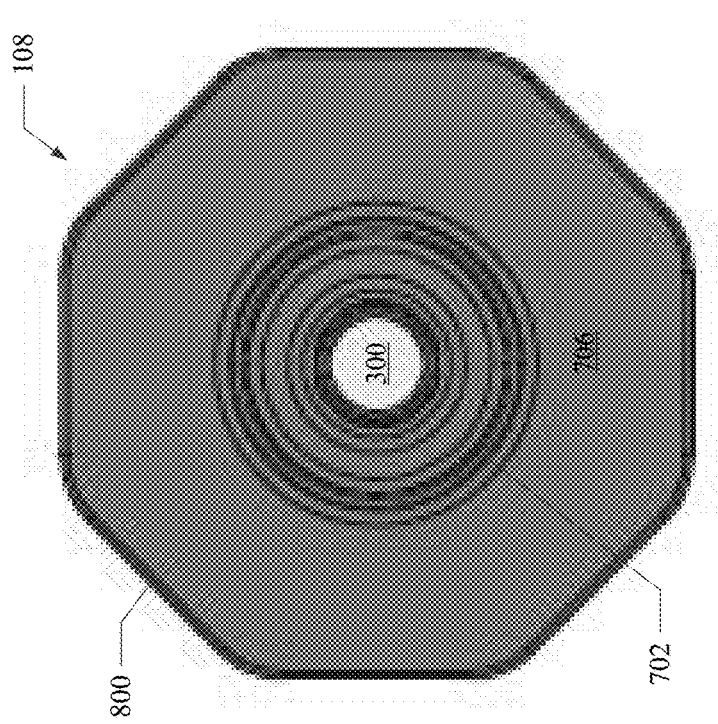
FIG. 8 depicts an end view of the proximal end of the suction sleeve of FIG. 1.

FIG. 7 is a cross-section of the proximal end 108 of an embodiment of the sleeve 100, and FIG. 8 is an end view of the proximal end 108. As illustrated by FIG. 7 and FIG. 8, the proximal end 108 of this embodiment of the sleeve 100 is ergonomically designed for use with the same hand that holds or controls the function of the suction instrument 400. As shown in FIG. 7, the proximal end 108 increases in diameter near the end of the sleeve 100. This increase in diameter mirrors the increases in diameter in a typical suction instrument 400 and can also make it easier for the surgeon to grasp and manipulate the sleeve 100. In embodiments, the exterior surface of the proximal end 108 can be rough, ridged or otherwise formed to allow the proximal end 108 to be easily gripped. In the illustrated embodiment, the proximal end 108 includes one or more internal annular shoulders 702 configured to couple with the one or more annular ledges 704 of the suction instrument 400, providing a travel stop that limits the movement of the inner cannula 402 within the sleeve 100. As shown in FIG. 7, the inner cannula 402 slides through the sleeve 100 until the annular ledge 704 of the suction instrument 400 abuts the annular shoulder 702 of the sleeve 100, limiting the amount by which the inner cannula 402 can extend past the distal end 104 of the sleeve 100.

In addition, the proximal end 108 of this embodiment of the sleeve 100 includes a flange 706 that allows a surgeon to control the position, rotation, and angle of the sleeve 100 relative to the body and to the suction instrument 400. The flange 706 is specifically configured to allow for manipulation in conjunction with the proximal end of the inner cannula 402 with one hand. The surgeon can slide the sleeve 100 with a single finger on either side of the flange 706 while still holding the suction instrument 400. As shown, the flange 706 has a larger diameter than the remainder of the proximal end 108 of the sleeve 100. By positioning a finger on the proximal end 108 in front of the flange 706 the surgeon can pull the sleeve 100 away from the distal tip of the inner cannula 402 by drawing the finger and flange 706 toward the proximal portion of the suction instrument 400. This movement will transition the suction instrument 400 and sleeve 100 from pool mode to spot mode. Conversely, by positioning a finger behind the flange 706 and the proximal end 108, the surgeon can transition the device into pool mode by pushing the finger and flange 706 forward, toward the distal tip of the inner cannula 402. This allows the surgeon to control the suction instrument 400 and alternate between pool and spot suction mode with one hand, without necessitating removal of the suction instrument 400 or sleeve 100 from the body.

FIG. 8 is an end view of an embodiment of the proximal end 108. Here, the flange 706 comprises a plurality of straight edge segments 800 annularly connected and configured about the proximal end 108 of the suction sleeve 100. The edge segments 800 provide corners or ridges that are easy for a surgeon to grip. In addition, the plurality of edge segments 800 allows the surgeon to rotate the sleeve 100 about the axis of the suction instrument 400. This feature can be particularly useful where the radial apertures 106 at the distal end 104 of the sleeve 100 are not evenly distributed around the circumference of the distal end 104. A configuration that includes apertures 106 only on one or more sides of the sleeve 100 can create a stronger, more directed suction or facilitate manufacturing. Rotation of the sleeve 100 allows the surgeon to control of this directed suction.

Figure 9:
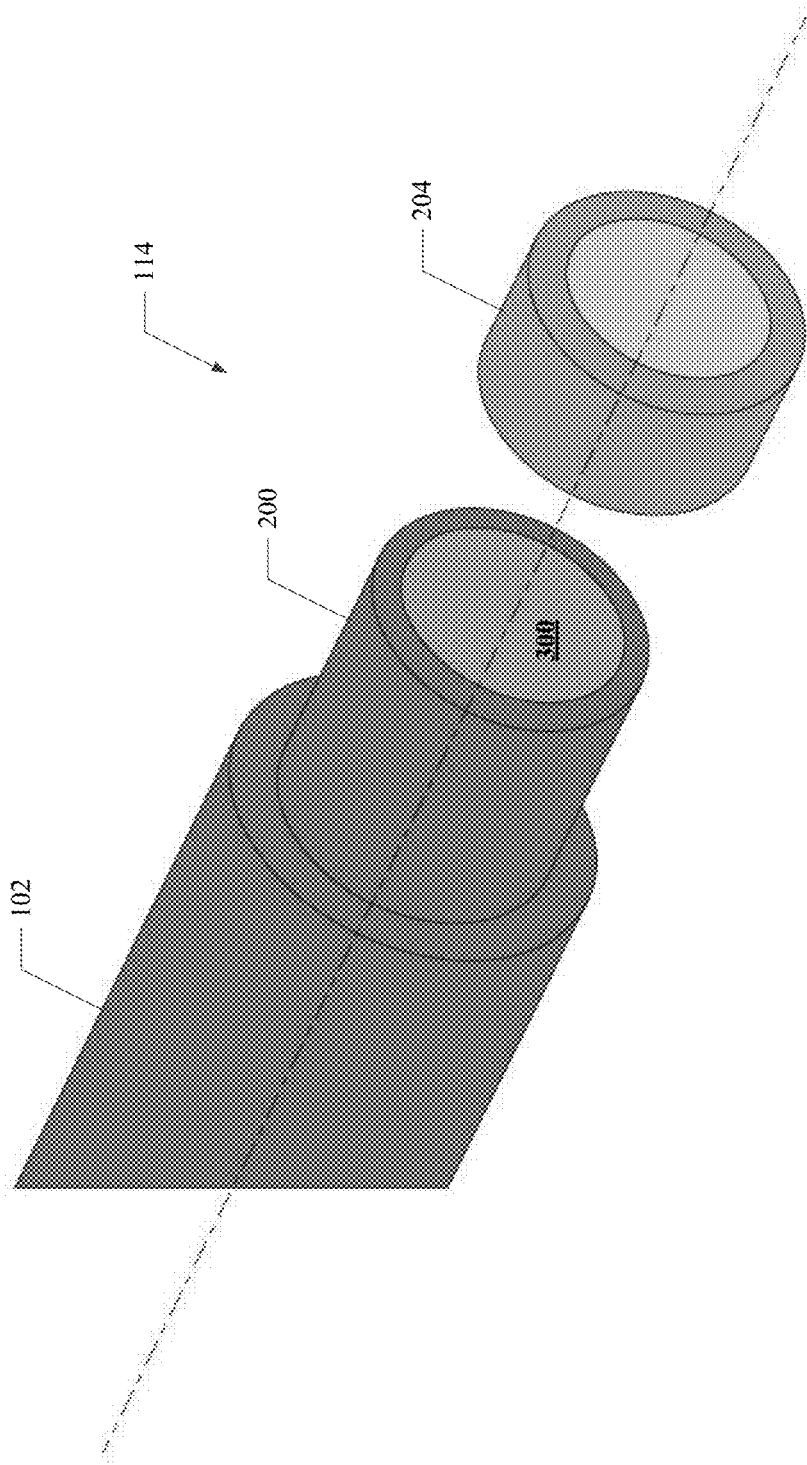
FIG. 9 depicts an enlarged perspective view of the inner connection member of the suction sleeve of FIG. 1 while disassembled.
Figure 10:
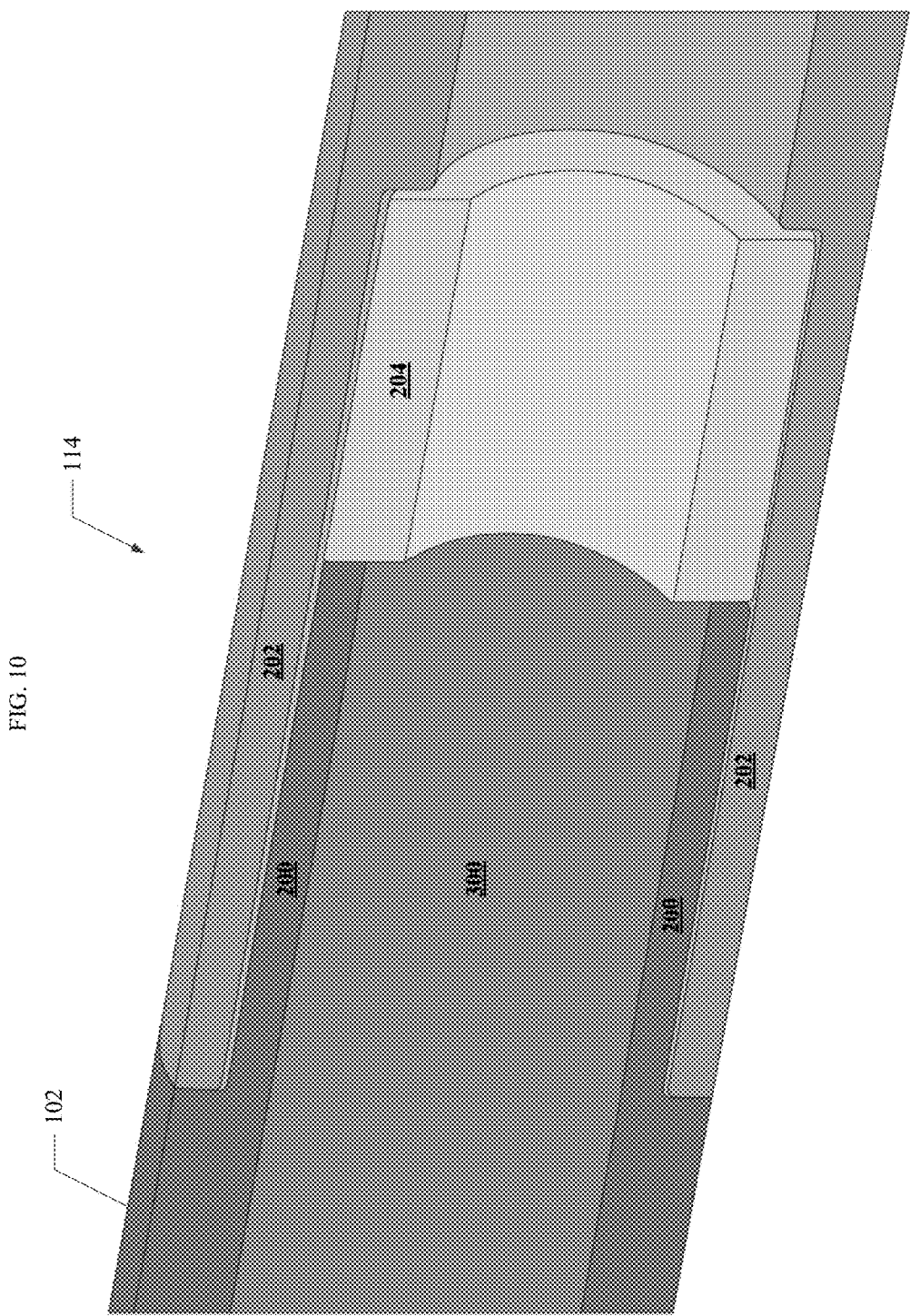
FIG. 10 depicts an enlarged sectional perspective view of the connector of the suction sleeve of FIG. 1 while assembled.

FIG. 9 and FIG. 10 provide a close view of an embodiment of a connector 114 that joins the segments 112 of the sleeve 100. As depicted, each connector 114 includes an inner connection member 200, outer connection member 202 and an O-ring 204. FIG. 9 is a perspective view of the disassembled connector 114, showing the O-ring 204 and inner connection member 200. The inner connection member 200 of this embodiment comprises a cylindrical portion with an outer diameter less than that of the tube 102 and an inner diameter substantially equal to that of the inner lumen 300. The outer connection member 202 of this embodiment, shown in FIG. 10, comprises a cylindrical portion with an outer diameter equal to that of the tube 102 and an inner diameter greater than that of the inner lumen 300 and approximately equal to, or slightly larger than, the outer diameter of the inner connection member 200, such that the inner connection member 200 can be inserted into the outer connection member 202. In embodiments, the inner connection member 200 is held in place within the outer connection member 202 via friction. In other embodiments, an adhesive is used to secure the inner and outer connection members 200, 202. In still other embodiments, this slip-fit connection, where the inner connection member 200 is inserted into the outer connection member 202, is secured via plastic welding, such as ultrasonic welding, hot gas welding, welding rod, heat sealing, freehand welding, speed tip welding, extrusion welding, contact welding, high frequency welding, hot plate welding, induction welding, injection welding, friction welding, spin welding, laser welding, transparent laser plastic welding, solvent welding, or any other suitable method for joining the connection members 200, 202.

In this embodiment, the connector 114 includes an O-ring 204 with an outer diameter generally equal to the outer diameter of the inner connection member 200 and an inner diameter approximately equal to, or slightly larger than, the outer diameter of the inner cannula 402 of the suction instrument 400. As illustrated by the cross-section of FIG. 10, when the embodiment of the sleeve 100 of FIG. 1 is assembled, the O-ring 204 sits within the outer connection member 202, held in place by the inner connection member 200.

Figure 11:
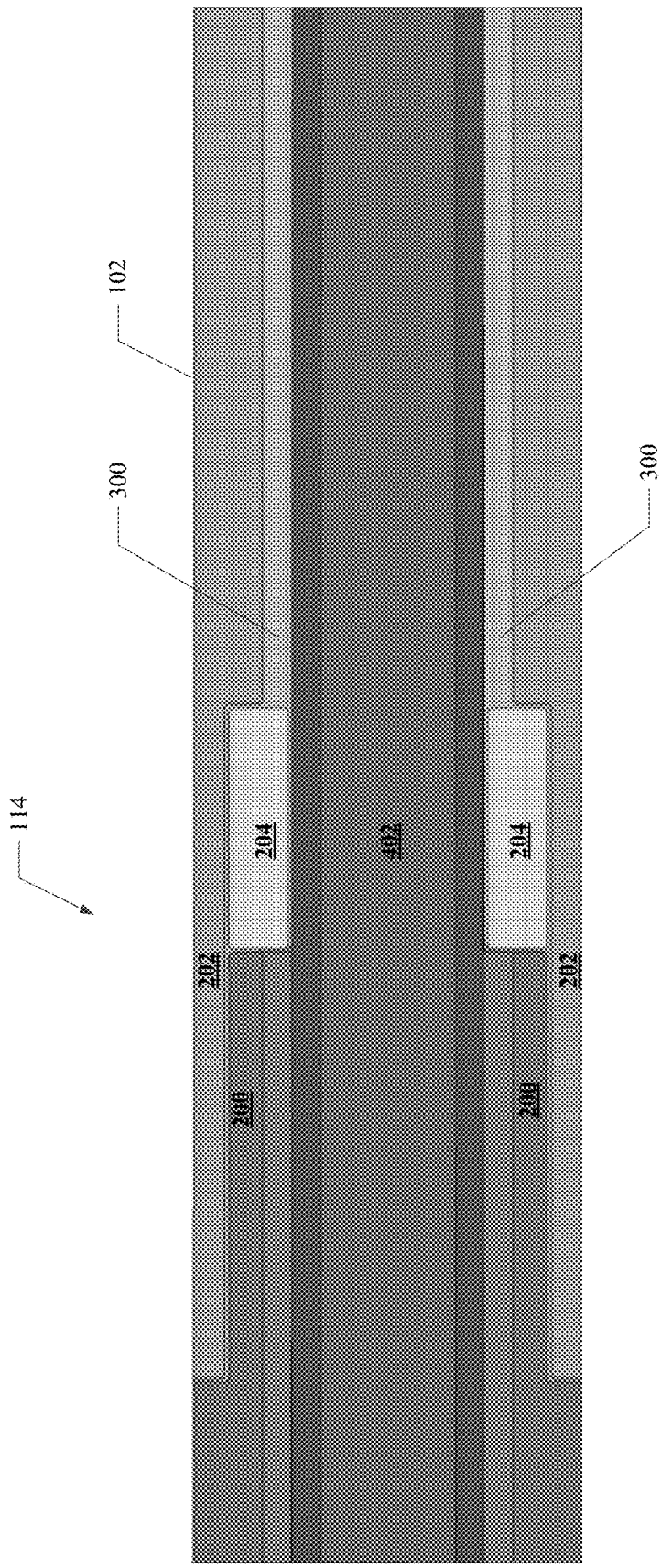
FIG. 11 depicts an enlarged sectional view of the connector of the suction sleeve of FIG. 1 while assembled and mounted on a suction instrument.
Figure 12:
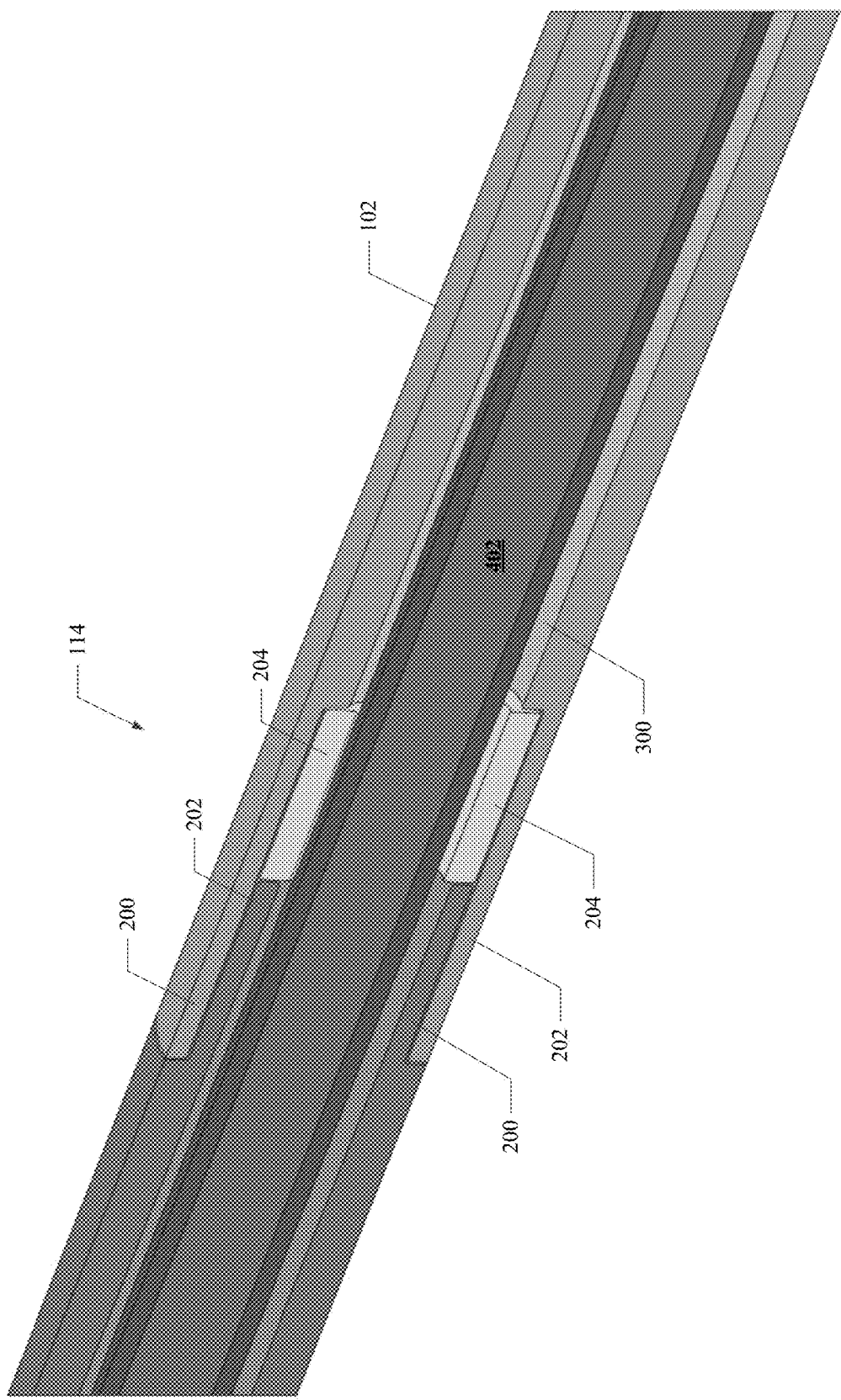
FIG. 12 depicts an enlarged sectional perspective view of the connector of the suction sleeve of FIG. 1 while assembled and mounted on a suction instrument.

FIG. 11 and FIG. 12 are cross-sections of an embodiment of a connector 114 that illustrate the manner in which the O-ring 204 of the connector 114 is generally configured to receive and support the inner cannula 402 within the inner lumen 300 of the sleeve 100. In addition, the O-ring 204 can provide a measure of resistance of the longitudinal movement or translation along the axis of the inner cannula 402 during use. This resistance can prevent accidental shifting between spot and pool mode. In embodiments, the O-ring 204 has an inner diameter approximately equal to, or even slightly smaller than, the diameter of the inner cannula 402. In embodiments, the O-ring is made of an elastic material that is capable of deforming to allow the inner cannula 402 to be inserted through the O-ring. The resistance created by the O-ring 204 allows for improved control over the movement and placement of the inner cannula 402 relative to the sleeve 100 while in use during surgery or other procedures, allowing the user to slide the inner cannula 402 to change between spot and pool suction. Additionally, in embodiments, the O-ring 204 creates a seal between the sleeve 100 and the inner cannula 402, which minimizes air loss during use and improves the ability of the sleeve 100 to function as a suction device.

Figure 13:
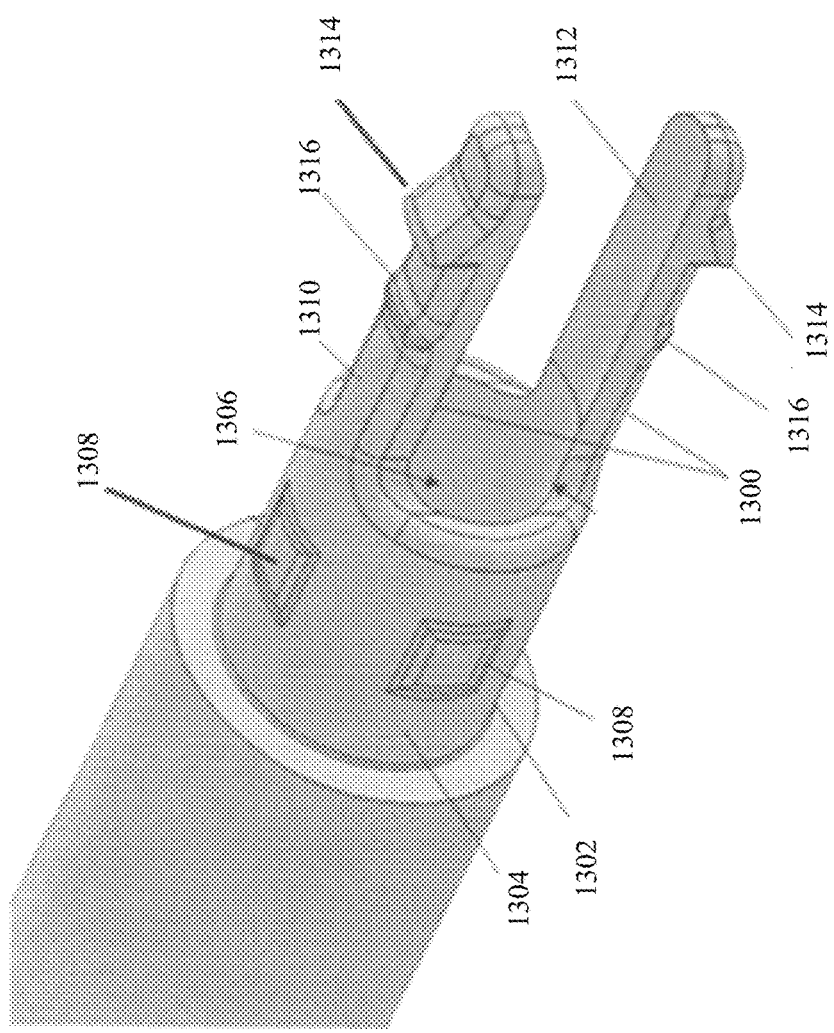
FIG. 13 depicts an enlarged perspective view of another embodiment of the connector of an embodiment of a suction sleeve while disassembled.
Figure 14:
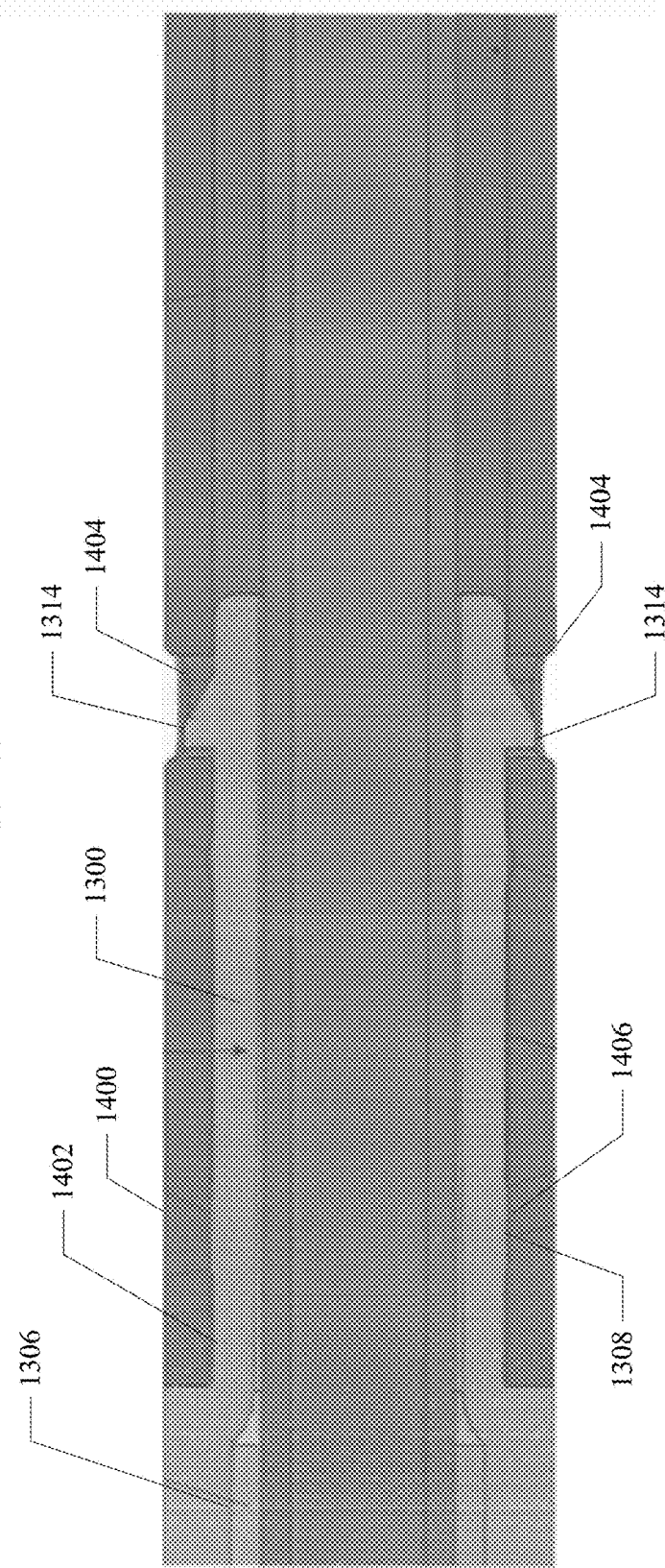
FIG. 14 depicts an enlarged sectional view of the connector of the suction sleeve of FIG. 13 while assembled.

FIG. 13 and FIG. 14, depict another embodiment of a connector 114 for joining segments 112 of a sleeve 100. In this embodiment, an inner connection member 200 includes a cylindrical portion 1302 and U-shaped tension fingers 1300 capable of bending inward of the cylindrical portion 1302. The cylindrical portion 1302 has an outer surface 1304 and an inner bore 1306. The outer surface 1304 may include one or more annularly spaced raised surface pads 1308. Each of the dual forward extending attachment fingers 1300 include an outer surface 1310 and an inner radial surface 1312. Each outer surface 1310 has an outward extending snap in catch 1314 and a raised surface pad 1316. The inner bore 1306 of the cylindrical portion 1302 and the inner radial surfaces 1312 of the U-shaped tension fingers 1300 form the guidance and resistance segment generally of a size and shape to receive and support the inner cannula 402 in a central manner relative to the sleeve 100 and provide resistance to the movement of the sleeve 100 along the axis of the inner cannula 402 during operation.

The outer connection member 202 couples with the inner connection member 200 connecting the first segment 112 with the second segment 112 of this embodiment of the sleeve 100. The outer connection member 202 generally comprises an outer surface 1400, an inner cylindrical surface 1402, and a pair of apertures 1404 configured to couple and fasten with the snap in catches 1314 of the inner connection member 200. The inner cylindrical surface 1402 may further include one or more annularly spaced catches 1406 corresponding and coupling with the one or more annularly spaced raised surfaces 1308 of the inner connection member 200 while in the fastened position. While in a fastened position, the inner cylindrical surface 1402 of the outer connection member 202 applies a downward force to each raised surface pads 1308 of the forward extending fingers 1300, thus urging the forward extending of the U-shaped tension fingers 1300 to squeeze the inner cannula 402 providing an improved grip and control.

In the embodiment of the sleeve 100 depicted by FIG. 13 and FIG. 14, the sleeve 100 further comprises a guidance and resistance segment which is generally configured to receive and support the inner cannula 402 centrally relative to the sleeve 100 and provide resistance to the movement of the sleeve 100 along the axis of the inner cannula 402 during operation. The resistance created by the guidance and resistance segment allows for improved control over the movement and placement of the inner cannula 402 relative to the sleeve 100 while in use during surgery or other procedures, allowing the user to readily slide the inner cannula 402 to change between spot and pool suction modes.

Figure 15:
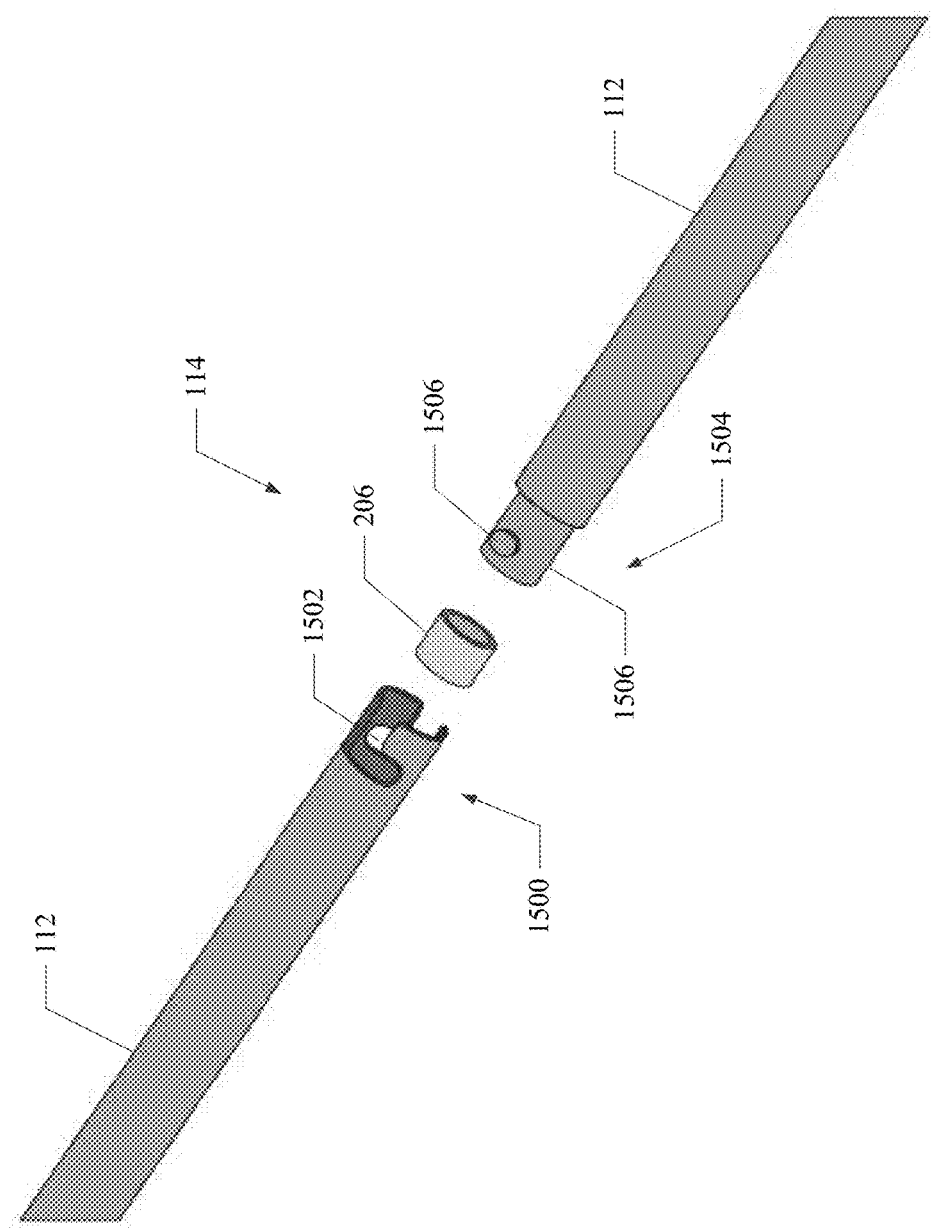
FIG. 15 depicts a perspective view of another embodiment of a connector of the suction sleeve.

FIG. 15 depicts another embodiment of a connector 114 for joining segments 112 of a sleeve 100. In this embodiment, the connector 114 is a bayonet connector. This embodiment of a connector 114 includes an outer connection member 1500, which includes one or more slots 1502, such as the depicted L-shaped slot 1502. The illustrated connector 114 also includes an inner connection member 1504 with an inner cylinder 1506 configured to insert into the outer connection member 1500, and one or more pegs 1508 that slide into the slot or slots 1502. As shown, the pegs 1508 are raised cylinders, but any suitable shape can be used. The connector 114 can secure the first segment 112 to the second segments 112 by sliding the pegs 1508 into the slots 1502 and rotating either the first or second segment 112.

FIG. 15 depicts a disassembled view of an embodiment of the connector 114. Here, an O-ring 204 can be inserted within the outer connection member 1500 prior to insertion of the inner connector member 1504. As discussed above, an O-ring 204 can help stabilize the inner cannula 402 within the sleeve 100 as well as forming a seal between the inner cannula 402 and the sleeve 100.

The sleeve 100 can be made in any manner and of any material chosen with sound engineering judgment. Preferably, materials will be strong, lightweight, long lasting, economic, and ergonomic. Construction of the sleeve 100 can be made of any known material known in the art of medical instrumentation such as synthetics, plastics and metals or a combination thereof.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes," "has" or "having" or variations in form thereof are used in either the detailed description or the claims, such terms are intended to be inclusive in a manner similar to the term "comprising" as "comprising" is interpreted when employed as a transitional word in a claim.

What is claimed is:
1. A sleeve for use with a minimally invasive surgery suction instrument, comprising:
   a tube having an inner lumen configured to receive an inner cannula of the suction instrument and allow the inner cannula to translate freely within the inner lumen, wherein the tube comprises a first segment and a second segment joined by a connector, the connector comprising:
      an outer connection member at the end of the first segment;
      an inner connection member at an end of the second segment and configured to insert into the outer connection member; and
      an O-ring seated within the outer connection member and configured to support the inner cannula of the suction instrument and form a seal between the inner cannula and the inner lumen;
   a distal end of the tube configured to insert into an introducer port, the distal end having a plurality of radially facing apertures and an axially facing opening; and
   a proximal end connected to the tube and configured to facilitate grasping and manipulation by a user to translate the sleeve between a first position exposing a distal tip of the inner cannula beyond the axially facing opening of the tube and a second position where the distal tip of the inner cannula is seated within the inner lumen of the tube, proximal to the radially facing apertures.

2. A sleeve for use with a minimally invasive surgery suction instrument, comprising:
- a tube having an inner lumen configured to receive an inner cannula of the suction instrument and allow the inner cannula to translate freely within the inner lumen, wherein the tube comprises a first segment and a second segment joined by a connector, wherein the connector comprises a slip-fit connection;
- a distal end of the tube configured to insert into an introducer port, the distal end having a plurality of radially facing apertures and an axially facing opening; and
- a proximal end connected to the tube and configured to facilitate grasping and manipulation by a user to translate the sleeve between a first position exposing a distal tip of the inner cannula beyond the axially facing opening of the tube and a second position where the distal tip of the inner cannula is seated within the inner lumen of the tube, proximal to the radially facing apertures.

3. A sleeve for use with a minimally invasive surgery suction instrument, comprising:
- a tube having an inner lumen configured to receive an inner cannula of the suction instrument and allow the inner cannula to translate freely within the inner lumen;
- a distal end of the tube configured to insert into an introducer port, the distal end having a plurality of radially facing apertures and an axially facing opening;
- a proximal end connected to the tube and configured to facilitate grasping and manipulation by a user to translate the sleeve between a first position exposing a distal tip of the inner cannula beyond the axially facing opening of the tube and a second position where the distal tip of the inner cannula is seated within the inner lumen of the tube, proximal to the radially facing apertures; and
- at least one channel on an exterior of the distal end of the sleeve, the channel connected to at least one of the plurality of apertures.

4. The sleeve of claim 3, wherein the channel is configured to direct flow of fluent material to at least one of the plurality of radially facing apertures.

5. A method of providing suction during a surgical procedure, comprising:
- providing a sleeve that slides onto an inner cannula of a suction instrument, the sleeve having:
  - a tube having an inner lumen configured to receive an inner cannula of the suction instrument and allow the inner cannula to translate freely within the inner lumen;
  - a distal end of the tube configured to insert into an introducer port, the distal end having a plurality of radially facing apertures and an axially facing opening, wherein the distal end of the sleeve includes a channel on an exterior of the distal end, the channel connected to at least one of the plurality of apertures; and
  - a proximal end configured to facilitate manipulation by a user;
- sliding the sleeve onto the inner cannula of the suction instrument, where the inner cannula is disposed within the inner lumen of the sleeve;
- inserting the distal end of the sleeve with the inner cannula through an introducer port into a body;
- manipulating the proximal end of the sleeve to extend the radial apertures over a distal tip of the inner cannula to provide pool mode suction; and
- manipulating the proximal end of the sleeve to extend the distal tip of the inner cannula beyond the distal end of the sleeve to transition to spot mode suction, where the transition between pool mode and spot mode occurs while the sleeve and suction instrument are seated within the introducer port.

6. The method of claim 5, further comprising directing fluent material to the at least one of the plurality of apertures via the channel.

7. A sleeve for use with a minimally invasive surgery suction instrument, comprising:
- a tube configured to slide over an inner cannula of the suction instrument;
- a distal end of the tube configured to insert into an introducer port, the distal end having a plurality of radially facing apertures and an axially facing opening;
- a proximal end of the tube configured to facilitate grasping and manipulation by a user, the proximal end having a flange that extends radially from the proximal end, wherein pressure on the flange slides the sleeve to cover the inner cannula of the suction instrument;
- a groove on an exterior of the distal end that directs flow of fluent material in the direction of at least one of the plurality of radially facing apertures; and
- an O-ring seated within the tube, wherein the inner cannula is inserted through the O-ring and the O-ring forms a seal between the inner cannula and interior surface of the tube.

8. The sleeve of claim 7, the tube comprising a first segment, a second segment, and a connector that couples a first segment of the tube and a second segment of the tube.

* * * * *